(12) United States Patent
Kameyama et al.

(10) Patent No.: US 11,432,534 B2
(45) Date of Patent: Sep. 6, 2022

(54) MONITORING APPARATUS AND PROGRAM

(71) Applicant: NTT DOCOMO, INC., Tokyo (JP)

(72) Inventors: Naoki Kameyama, Tokyo (JP); Tomoe Ushiro, Tokyo (JP); Youhei Oono, Tokyo (JP); Yuichiro Segawa, Tokyo (JP)

( * ) Notice: Subject to any disclaimer, the term of this patent is extended or adjusted under 35 U.S.C. 154(b) by 39 days.

(21) Appl. No.: 17/056,833

(22) PCT Filed: May 8, 2019

(86) PCT No.: PCT/JP2019/018399
§ 371 (c)(1),
(2) Date: Nov. 19, 2020

(87) PCT Pub. No.: WO2019/225313
PCT Pub. Date: Nov. 28, 2019

(65) Prior Publication Data
US 2021/0204522 A1    Jul. 8, 2021

(30) Foreign Application Priority Data

May 23, 2018   (JP) .............................. JP2018-098944

(51) Int. Cl.
*A01K 29/00*      (2006.01)
*B64C 13/18*      (2006.01)
*B64C 39/02*      (2006.01)
*B64D 47/08*      (2006.01)

(52) U.S. Cl.
CPC ............ *A01K 29/005* (2013.01); *B64C 13/18* (2013.01); *B64C 39/024* (2013.01); *B64D 47/08* (2013.01); *B64C 2201/027* (2013.01); *B64C 2201/127* (2013.01); *B64C 2201/141* (2013.01)

(58) Field of Classification Search
None
See application file for complete search history.

(56) References Cited

U.S. PATENT DOCUMENTS

| 2017/0202185 A1* | 7/2017 | Trumbull ........... A61B 5/14507 |
| 2018/0027772 A1* | 2/2018 | Gordon ................. G05D 1/104 |
| 2018/0049407 A1* | 2/2018 | Castelli ............... A01K 11/008 |

(Continued)

FOREIGN PATENT DOCUMENTS

JP    2017206072 A    11/2017

OTHER PUBLICATIONS

International Search Report issued in corresponding PCT Application No. PCT/JP2019/018399 dated Jul. 16, 2019, 2 pages.

*Primary Examiner* — Heather R Jones
(74) *Attorney, Agent, or Firm* — MKG, LLC (57) ABSTRACT

When utilizing a flying vehicle to monitor an animal that is grazing, the stress of the animal targeted for monitoring is mitigated. An acquisition unit acquires position information indicating the position of an animal that is grazing. A determination unit determines the reactivity of the animal to the approach of a flying vehicle. A setting unit sets a distance that depends on the determined reactivity. An instruction unit instructs the flying vehicle to start flying toward a monitoring position corresponding to the position indicated by the acquired position information and the set distance, and to perform processing for monitoring the animal on the basis of the monitoring position.

20 Claims, 7 Drawing Sheets

(56) References Cited

U.S. PATENT DOCUMENTS

2018/0279583 A1* 10/2018 Yajima ................. A01K 11/008
2018/0310526 A1* 11/2018 Birch .................... A01M 29/00
2020/0154694 A1* 5/2020 Santana ............... A01K 15/023

* cited by examiner

| IDENTIFICATION INFORMATION | POSITION INFORMATION | BIOLOGICAL INFORMATION |
|---|---|---|
| ANIMAL A | P1 | M1 |
| ANIMAL B | P2 | M2 |
| ANIMAL C | P3 | M3 |
| ANIMAL D | P4 | M4 |
| . . . | . . . | . . . |

| IDENTIFICATION INFORMATION | DEGREE OF ABNORMALITY |
|---|---|
| ANIMAL A | 6 |
| ANIMAL B | 4 |
| ANIMAL C | 4 |
| ANIMAL D | 6 |
| . . . | . . . |

| REACTIVITY | ALTITUDE [M] |
|---|---|
| HIGH | 70 |
| LOW | 30 |

MONITORING APPARATUS AND PROGRAM

TECHNICAL FIELD

The present invention relates to a technology for using a flying vehicle to monitor animals.

BACKGROUND

Technologies for performing monitoring using a flying vehicle such as a drone are known. In this monitoring, the flying vehicle may approach the ground. For example, JP-2017-206072A describes an unmanned aerial vehicle descending after a descending course is determined, based on an object in a descent target region.

In the case of using a flying vehicle to monitor animals, there is a risk of the animals being spooked by the flying vehicle and acting in an unexpected manner. Animals that have a heightened reactivity to the approach of such a flying vehicle will be stressed when not monitored from a greater distance than normal. However, with the technology described in JP-2017-206072A, the flying vehicle descends without regard for the reactivity of the animals to the approach of the flying vehicle, thus possibility stressing the animals.

SUMMARY OF INVENTION

An object of the present invention is to mitigate the stress of animals targeted for monitoring, when utilizing a flying vehicle to monitor grazing animals.

The present invention provides a monitoring apparatus provided with an acquisition unit that acquires position information indicating a position of an animal that is grazing, a determination unit that determines a reactivity of the animal to an approach of a flying vehicle, a setting unit that sets a distance that depends on the determined reactivity, and an instruction unit that instructs the flying vehicle to start flying toward a monitoring position corresponding to the position indicated by the acquired position information and the set distance, and to perform processing for monitoring the animal on a basis of the monitoring position.

Also, the present invention provides a program for causing a computer to execute a step of acquiring position information indicating a position of an animal that is grazing, a step of determining a reactivity of the animal to an approach of a flying vehicle, a step of setting a distance that depends on the determined reactivity, and a step of instructing the flying vehicle to start flying toward a monitoring position corresponding to the position indicated by the acquired position information and the set distance, and to perform processing for monitoring the animal on a basis of the monitoring position.

According to the present invention, the stress of animals targeted for monitoring can be mitigated, when utilizing a flying vehicle to monitor grazing animals.

DETAILED DESCRIPTION

1. Configuration

Figure 1:
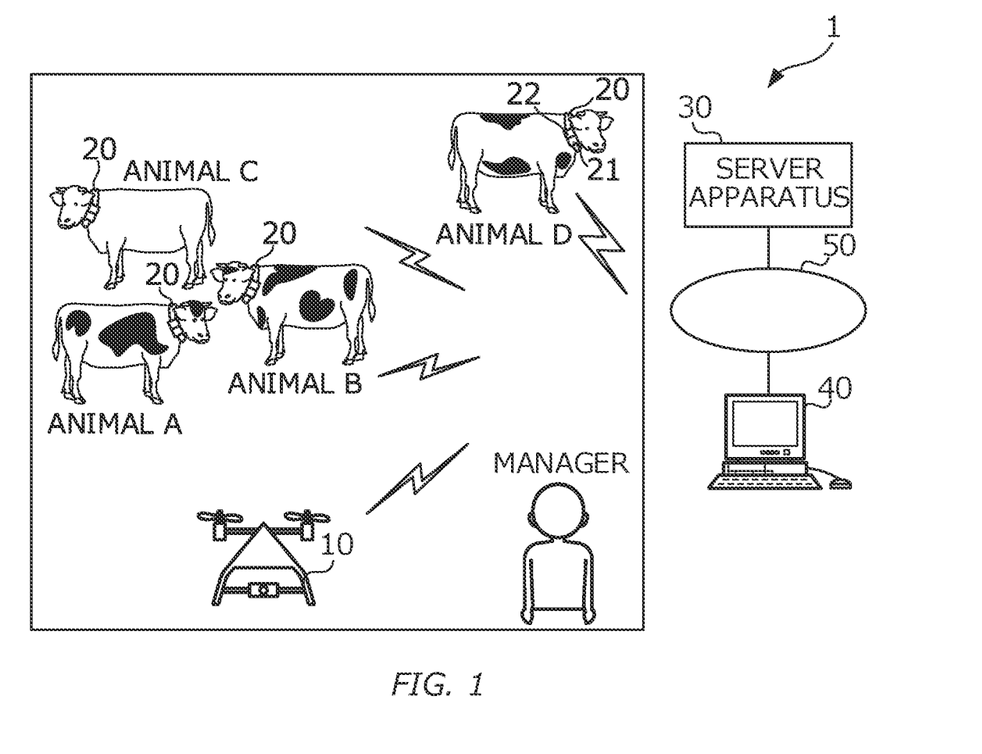
FIG. 1 is a diagram showing an example of a configuration of monitoring system 1 according to an embodiment, in accordance to the present invention.

FIG. 1 is a diagram showing an example of a configuration of monitoring system 1 according to the present embodiment. In this example, a plurality of animals are grazing in a place such as a farm. This "grazing" refers to animals being allowed to roam freely in a controlled environment. The grazing animals may be any type of animal, such as cows, sheep, horses, sheep, and goats, for example. Also, only one type of animal may be grazed, or a plurality of types of animal may be grazed. These animals are under the control of a manager. Monitoring system 1 is a system that monitors the grazing animals. Monitoring system 1 is provided with flying vehicle 10, a plurality of sensor apparatuses 20, server apparatus 30, and terminal apparatus 40. Note that the number of apparatuses shown in FIG. 1 is illustrative, and is not limited thereto.

Flying vehicle 10, the plurality of sensor apparatuses 20, server apparatus 30 and terminal apparatus 40 are connected via communication line 50. Communication line 50 includes a wireless network and the Internet, for example, and transmits communication between these apparatuses.

Figure 2:
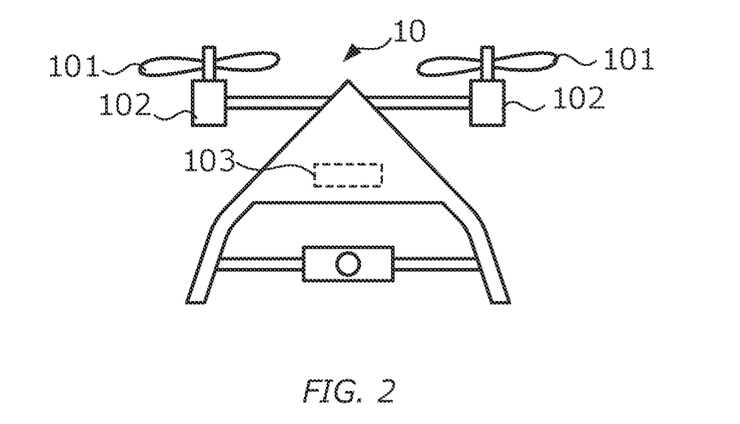
FIG. 2 is a diagram showing an example of an outward appearance of flying vehicle 10, in accordance to the present invention.

FIG. 2 is a diagram showing an example of an outward appearance of flying vehicle 10. Flying vehicle 10 is an unmanned aerial vehicle capable of flying autonomously even when not manually operated. Flying vehicle 10 may be a drone, for example. Flying vehicle 10 is provided with propellers 101, drive apparatus 102, and battery 103. Propellers 101 rotate about an axis. Flying vehicle 10 flies due to propellers 101 rotating. Drive apparatus 102 provides power to rotate propellers 101. Drive apparatus 102 is a motor, for example. Drive apparatus 102 may be directly connected to propellers 101, or may be connected to propellers 101 via a transmission mechanism that transmits the power of drive apparatus 102 to propellers 101. Battery 103 supplies electric power to various components of flying vehicle 10 including drive apparatus 102.

Figure 3:
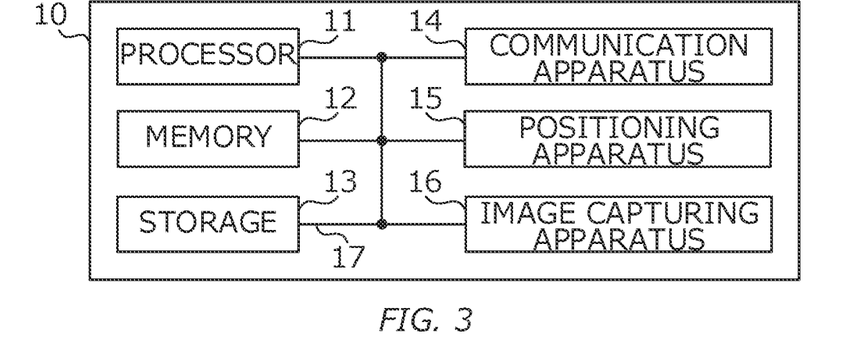
FIG. 3 is a diagram showing a hardware configuration of flying vehicle 10, in accordance to the present invention.

FIG. 3 is a diagram showing a hardware configuration of flying vehicle 10. Flying vehicle 10, physically, may be constituted as a computer apparatus including processor 11, memory 12, storage 13, communication apparatus 14, positioning apparatus 15, image capturing apparatus 16, and bus 17. Note that, in the following description, the word "apparatus" can be replaced by circuit, device, unit, and the like.

Processor 11 operates an operating system to perform overall control of a computer, for example. Processor 11 may be constituted by a central processing unit (CPU) including an interface with a peripheral apparatus, a control apparatus, a computational apparatus, and a register. Also, processor 11 reads out a program (program code), a software module and data from storage 13 and/or communication apparatus 14 to memory 12, and executes various types of processing in accordance therewith. A program that causes a computer to execute at least some of the operations of flying vehicle 10 is used as the program. The various types of processing that are executed in flying vehicle 10 may be executed by one processor 11 or may be executed simultaneously or sequentially by two or more processors 11. Processor 11 may be implemented with one or more chips. Note that the program may be transmitted from a network via a telecommunication line.

Memory 12 is a computer-readable recording medium, and may be constituted by, for example, at least one of a ROM (Read Only Memory), an EPROM (Erasable Programmable ROM), an EEPROM (Electrically Erasable Programmable ROM), and a RAM (Random Access Memory). Memory 12 may be referred to as a register, a cache, a main memory (main storage apparatus), and the like. Memory 12 is able to save an executable program (program code), a software module and the like in order to implement a monitoring method according to one embodiment of the present invention.

Storage 13 is a computer-readable recording medium, and may be constituted by, for example, at least one of an optical disk such as CD-ROM (Compact Disc ROM), a hard disk drive, a flexible disk, a magneto-optical disk (e.g., compact disk, digital versatile disk, Blu-ray (registered trademark) disk), a smart card, a flash memory (e.g., card, stick, key drive), a floppy (registered trademark) disk, and a magnetic strip. Storage 13 may be referred to as an auxiliary storage apparatus.

Communication apparatus 14 is hardware (transceiver device) for performing communication with a computer via a cable and/or a wireless network, and may, for example, also be referred to as a network device, a network controller, a network card, a communication module, and the like.

Positioning apparatus 15 measures the position of flying vehicle 10 at a predetermined time interval. Positioning apparatus 15 is a GPS (Global Positioning System) receiver, for example, and measures the current position of flying vehicle 10 based on GPS signals received from a plurality of satellites. This position may be indicated using latitude, longitude, and altitude, for example.

Image capturing apparatus 16 is provided facing the ground in a position at which images of animals on the ground can be shot in flight in flying vehicle 10, such as a position opposing the ground in flight, for example. Image capturing apparatus 16 is a camera, for example, and shoots images by joining images of the subject on an image sensor, using an optical system. This image may be a still image or may be a moving image. Note that image capturing apparatus 16 is not limited to a visible light camera that shoots visible light images. For example, image capturing apparatus 16 may include an infrared camera that shoots heat distribution images referred to as thermography.

Also, apparatuses such as processor 11 and memory 12 are connected by bus 17 which is for communicating information. Bus 17 may be constituted by a single bus or may be constituted by buses that differ between apparatuses.

Returning to FIG. 1, sensor apparatus 20 is a compact apparatus that has a wireless communication function, and is attached to each animal that is grazing. For example, in the case where the animals are wearing a collar, sensor apparatus 20 may be attached to the collar. Sensor apparatus 20 is provided with positioning apparatus 21 and biological information sensor 22. Positioning apparatus 21 is a similar apparatus to above-described positioning apparatus 15, and measures the position of the animal at a predetermined time interval. Biological information sensor 22 detects biological information of the animal. This "biological information" refers to information emitted by a living body. This biological information may include body temperature, heart rate, pulse rate or breathing rate, for example.

Figure 4:
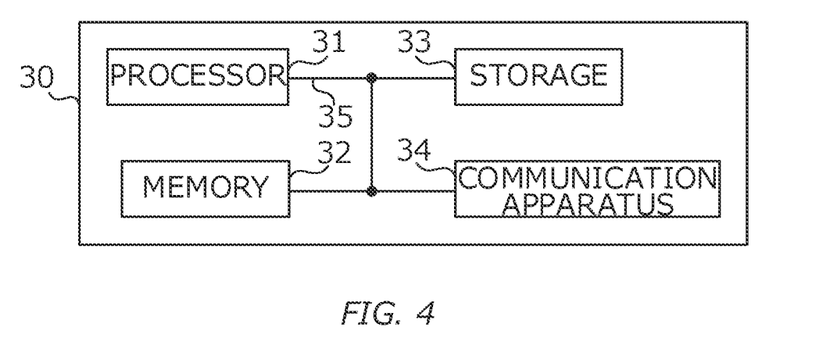
FIG. 4 is a diagram showing a hardware configuration of server apparatus 30, in accordance to the present invention.

FIG. 4 is a diagram showing the hardware configuration of server apparatus 30. Server apparatus 30, physically, may be constituted as a computer apparatus that includes processor 31, memory 32, storage 33, communication apparatus 34, and bus 35. Since processor 31, memory 32, storage 33, communication apparatus 34 and bus 35 are respectively similar to processor 11, memory 12, storage 13, communication apparatus 14 and bus 17 that were described above, description thereof is omitted.

Figure 5:
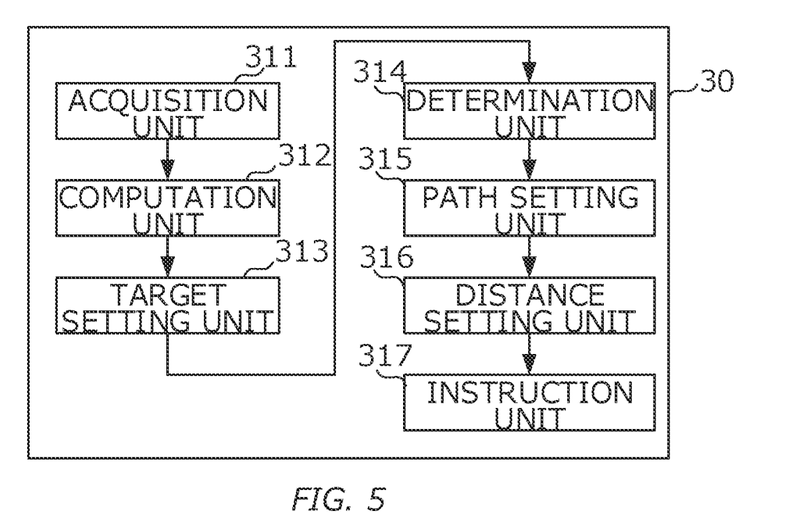
FIG. 5 is a diagram showing an example of a functional configuration of server apparatus 30, in accordance to the present invention.

FIG. 5 is a diagram showing an example of a functional configuration of server apparatus 30. Server apparatus 30 functions as acquisition unit 311, computation unit 312, target setting unit 313, determination unit 314, path setting unit 315, distance setting unit 316, and instruction unit 317. These functions are realized by processor 31 performing computational operations, and controlling communication by communication apparatus 34 and readout and/or writing of data in memory 32 and storage 33, due to predetermined software (programs) being loaded to hardware such as processor 31 and memory 32.

Acquisition unit 311 acquires position information indicating the position of an animal that is grazing and state information indicating the state of the animal. This position information is information indicating a position measured by positioning apparatus 21, for example. The state information is biological information detected by biological information sensor 22, for example. The position information and state information may be sent from sensor apparatus 20, for example.

Computation unit 312 computes the degree of abnormality of an animal. This "degree of abnormality" refers to a value indicating the possibility of there being an abnormality with the animal. A higher degree of abnormality indicates a greater possibility of there being an abnormality with the animal. This degree of abnormality may be computed based on the position information or the biological information acquired by acquisition unit 311. For example, computation unit 312 may raise the degree of abnormality, in the case where it is judged that the animal has carried out a predetermined action or where it is judged that this predetermined action has been carried out for a predetermined time, based on the position information acquired by acquisition unit 311. This predetermined action is an abnormal action that differs from a normal action, such as being separated from the group or staying in the one place. The predetermined time is a time for which it is regarded that the abnormal action is continuous, rather than being a temporary action, for example. Also, computation unit 312 may raise the degree of abnormality, in the case where it is judged that the animal is in a predetermined state or where it is judged that this predetermined state has continued for a predetermined time, based on the state information acquired by acquisition unit 311. This predetermined state is an abnormal state that differs from a normal state, such as body temperature being higher than normal, for example. The predetermined time is a time for which it is regarded that the abnormal state is ongoing, rather than being a temporary state, for example. Also, individual differences between animals may be reflected in the judgment of whether the animal is in a predetermined state. For example, it may be judged, on the basis of the normal temperature of each animal, whether the body temperature of the animal is high. Note that "computation" refers to obtaining the degree of abnormality, and does not necessarily involve a calculation. Also, the degree of abnormality is not necessarily a numerical value.

Target setting unit 313 sets an animal whose degree of abnormality computed by computation unit 312 is greater than or equal to a threshold value as a monitoring target. This threshold value is a value at which the possibility of an abnormality is considered to be high, for example, and is set in advance.

Determination unit 314 determines the reactivity of an animal to the approach of flying vehicle 10. This "reactivity" refers to a value indicating the tendency of the animal to react to the approach of flying vehicle 10, such as being spooked. A higher reactivity indicates a greater tendency to react to the approach of flying vehicle 10. This "approach" refers to getting close to an animal. For example, it can be said that flying vehicle 10 is approaching an animal, when flying vehicle 10 is within a predetermined range from the position of the animal. This predetermined range may be a range in which the animal can perceive flying vehicle 10, for example. This reactivity may be determined according to the type of animal or the degree of the familiarity of the animal to flying vehicle 10. This degree of familiarity may be higher as the number or times that flying vehicle 10 has approached the animal in the past or the elapsed time since the animal came to the place where it is grazing increases. The reactivity may be lower as the degree of familiarity increases.

Path setting unit 315 sets a flight path toward a monitoring position corresponding to the position of the animal targeted for monitoring set by target setting unit 313, based on the position information acquired by acquisition unit 311. At this time, a difference flight path may be set according to whether the animal targeted for monitoring is within a predetermined range from a predetermined place. For example, in the case where it is judged that the animal targeted for monitoring is within the predetermined range from the predetermined place, a flight path toward the monitoring position from a different direction to the direction toward the predetermined place from the position of the animal may be set. A place into which it is desirable to prevent the animal from entering, such as a dangerous place or someone else's property, for example, may be determined in advanced as this predetermined place. This predetermined range is a range close to the predetermined place and from which it is possible to moving quickly into the predetermined place, for example. Note that, in the case where the airspace through which flying vehicle 10 flies is divided into a plurality of cells, for example, the flight path may be represented by a plurality of continuous cells.

Distance setting unit 316 sets a distance that depends on the reactivity computed by determination unit 314. For example, the distance may be longer as the reactivity increases. Also, in the case where the path toward the monitoring position passes through a predetermined range from another animal, distance setting unit 316 may set a distance that further depends on the reactivity of the other animal. This predetermined range may be a range in which the animal can perceive flying vehicle 10, for example. These distances may, for example, be a distance from the ground, that is, a height from the ground.

Instruction unit 317 instructs flying vehicle 10 to start flying toward the monitoring position corresponding to the position indicated by the position information acquired by acquisition unit 311 and the distance set by distance setting unit 316, along the flight path set by path setting unit 315, and to perform processing for monitoring the animal on the basis of the monitoring position. This monitoring position is a position serving as a basis for when shooting an image of the animal targeted for monitoring, for example, and may be a position that is a set distance above the position indicated by the position information acquired by acquisition unit 311. The monitoring position and the image shooting position may be different. In this case, flying vehicle 10 moves to the image shooting position from the monitoring position when shooting an image, and return to the monitoring position again when image shooting has finished. The processing for monitoring an animal is processing for shooting an image of the animal, for example. Instructions may be given to flying vehicle 10 by transmitting instruction information to flying vehicle 10, for example.

Figure 6:
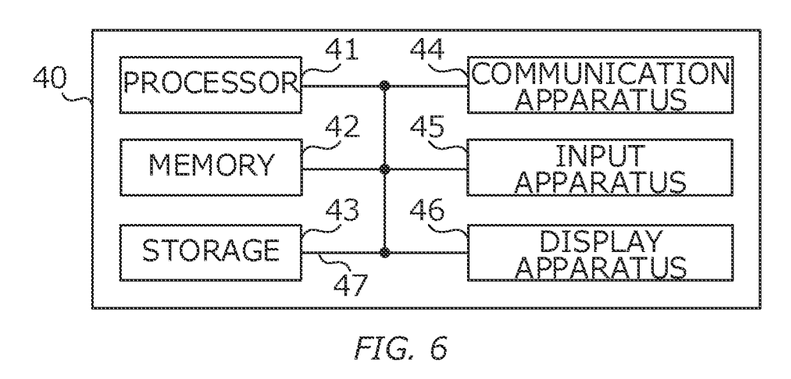
FIG. 6 is a diagram showing a hardware configuration of terminal apparatus 40, in accordance to the present invention.

FIG. 6 is a diagram showing the hardware configuration of terminal apparatus 40. Terminal unit 40, physically, may be constituted as a computer apparatus that includes processor 41, memory 42, storage 43, communication apparatus 44, input apparatus 45, display apparatus 46, and bus 47. Since processor 41, memory 42, storage 43, communication apparatus 44 and bus 47 are respectively similar to processor 11, memory 12, storage 13, communication apparatus 14 and bus 17 that were described above, description thereof is omitted. Input apparatus 45 is used for inputting various types of information. For example, input apparatus 45 is an input device (e.g., keyboard, mouse, microphone, switch, button, sensor, etc.) that receives input from outside. Display apparatus 46 is an output device (e.g., display) that implements external output. For example, display apparatus 46 may be constituted to include a liquid crystal display. Note that input apparatus 45 and display apparatus 46 may have an integrated configuration (e.g., touch panel).

2. Operations 2.1 Data Collection Processing Here, as shown in FIG. 1, the case where animals A to D are included among a plurality of animals is assumed. Sensor apparatuses 20 each transmit position information indicating the current position of an animal measured by positioning apparatus 21 and biological information of the animal detected by biological information sensor 22 to server apparatus 30 at a predetermined time interval, together with the identification information of the animal. Server apparatus 30 receives the information transmitted from sensor apparatuses 20 with acquisition unit 311, and stores the received information in storage 33.

Figure 7:
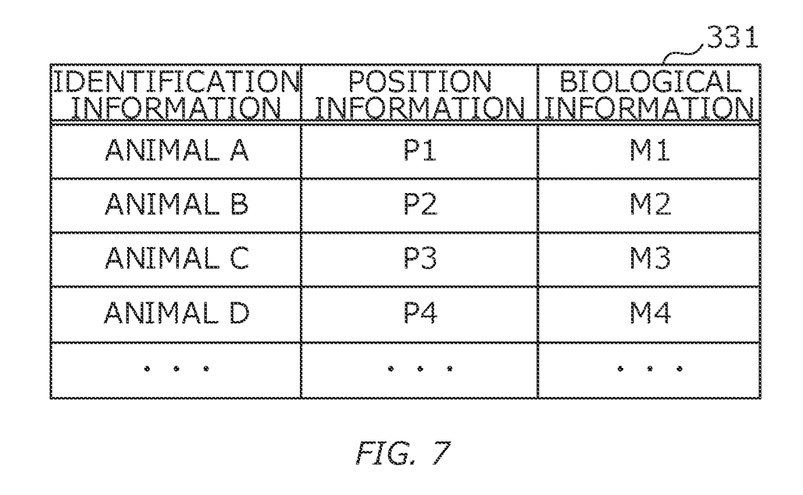
FIG. 7 is a diagram showing an example of database 331 stored in storage 33, in accordance to the present invention.

FIG. 7 is a diagram showing an example of database 331 stored in storage 33. Database 331 includes identification information, position information and biological information received from sensor apparatuses 20. These pieces of information are stored in association with each other. For example, in the case where identification information, position information "P1" and biological information "M1" of animal A are received from sensor apparatus 20, these pieces of information are stored in association with each other, as shown in FIG. 7. Database 331 thus accumulates information transmitted from each sensor apparatus 20.

Figure 8:
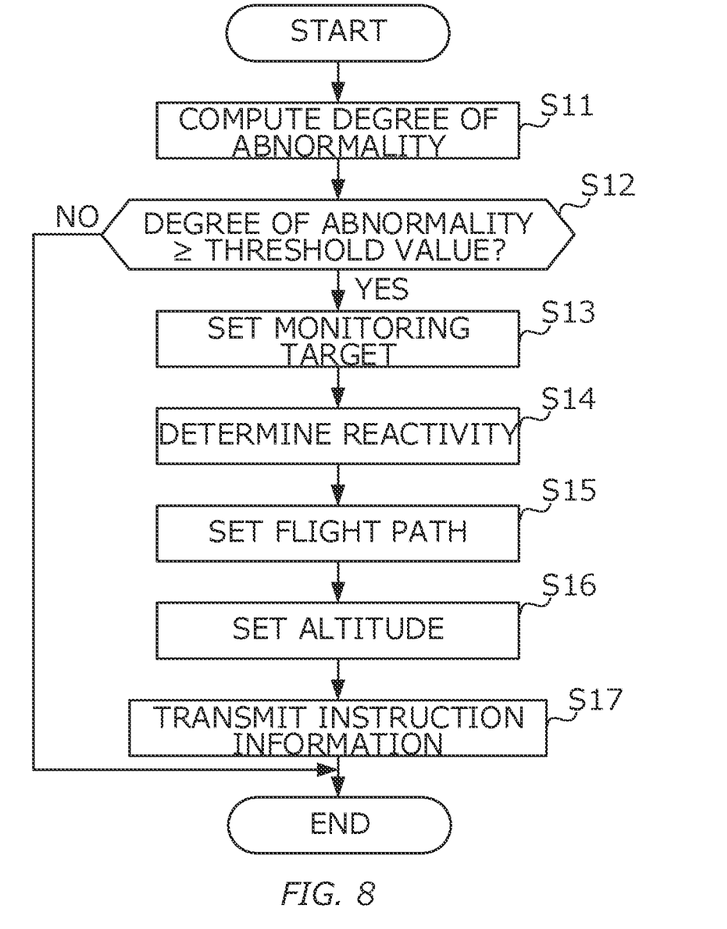
FIG. 8 is a flowchart showing an example of monitoring processing that is performed by server apparatus 30, in accordance to the present invention.

2.2 Monitoring Processing FIG. 8 is a flowchart showing an example of monitoring processing that is performed by server apparatus 30. This processing may be started at a predetermined time interval, or may be started when new information is stored in database 331, for example.

Computation unit 312 computes the degree of abnormality of each animal, based on database 331 (step S11). In this example, the degree of abnormality is shown using numbers 1 to 10. A larger number indicates a higher degree of abnormality.

Figure 9:
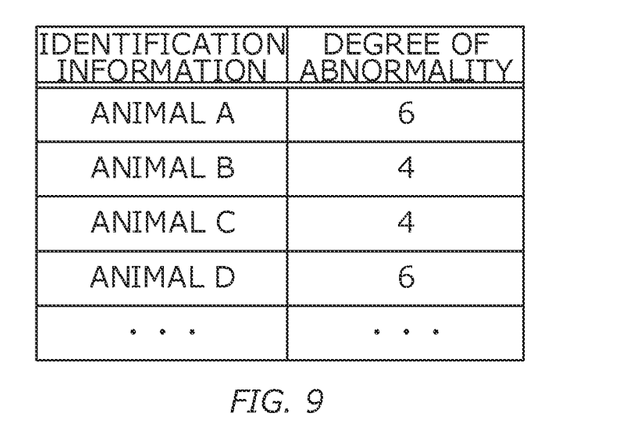
FIG. 9 is a diagram showing an example of the degree of abnormality of each animal, in accordance to the present invention.

FIG. 9 is a diagram showing an example of the degree of abnormality of each animal. First, computation unit 312 judges, for each animal, whether the animal has carried out a predetermined action or is in a predetermined state, based on the contents stored in database 331. Assume the case where animals A to C are grouped together, and, furthermore, where animal D is separated from this group, based on position information "P1" to "P4" of animals A to D stored in database 331, for example. For example, in the case where animal D remains separated from the group for a predetermined time, the degree of abnormality of animal D may be raised to "6" from the current degree of abnormality. Also, assume the case where it is judged that the body temperature of animal A is higher than normal, based on biological information "M1" of animal A stored in database 331, for example. For example, in this case, the degree of abnormality of animal A may be raised to "6" from the current degree of abnormality.

Target setting unit 313 judges, for every animal, whether the degree of abnormality computed in step S11 is greater than or equal to a threshold value (step S12). For example, if all the degrees of abnormality are less than the threshold value (judgment of step S12 is NO), this processing is ended. On the other hand, as shown in FIG. 9, if the degree of abnormality of animal D is "6" and the threshold value is "5", it is judged that the degree of abnormality is greater than or equal to the threshold value (judgment of step S12 is YES). In this case, target setting unit 313 sets the animal whose degree of abnormality is greater than or equal to the threshold value as the monitoring target (step S13). For example, in the case where the degree of abnormality of animal D is greater than or equal to the threshold value, animal D is set as the monitoring target.

Determination unit 314 determines, for every animal, the reactivity to the approach of flying vehicle 10 (step S14). For example, in the case where the type of animal is "horse" or "sheep", a reactivity "high" may be determined. On the other hand, in the case where the type of animal is "cow", a reactivity "low" may be determined. Also, in the case where flying vehicle 10 approaches an animal for the first time, the reactivity "high" may be determined, since the degree of familiarity of the animal to flying vehicle 10 will be less than or equal to a predetermined degree. On the other hand, in the case where flying vehicle 10 has approached the animal a number of times in the past, and the degree of familiarity of the animal to flying vehicle 10 is higher than the predetermined degree, the reactivity "low" may be determined.

Path setting unit 315 sets a flight path toward a monitoring position corresponding to the position of the animal targeted for monitoring set in step S13, based on the position information stored in database 331 (step S15). At this time, distance setting unit 316 determines whether the animal targeted for monitoring is within a predetermined range from a predetermined place such as a cliff. In the case where it is judged that the animal targeted for monitoring is not within the predetermined range from the predetermined place, the shortest flight path toward the monitoring position from the current position of flying vehicle 10 is set, for example. On the other hand, in the case where it is judged that the animal targeted for monitoring is within the predetermined range from the predetermined place, a flight path toward the monitoring position from a different direction to the direction toward the predetermined place from the position of the animal targeted for monitoring is set.

Figure 10:
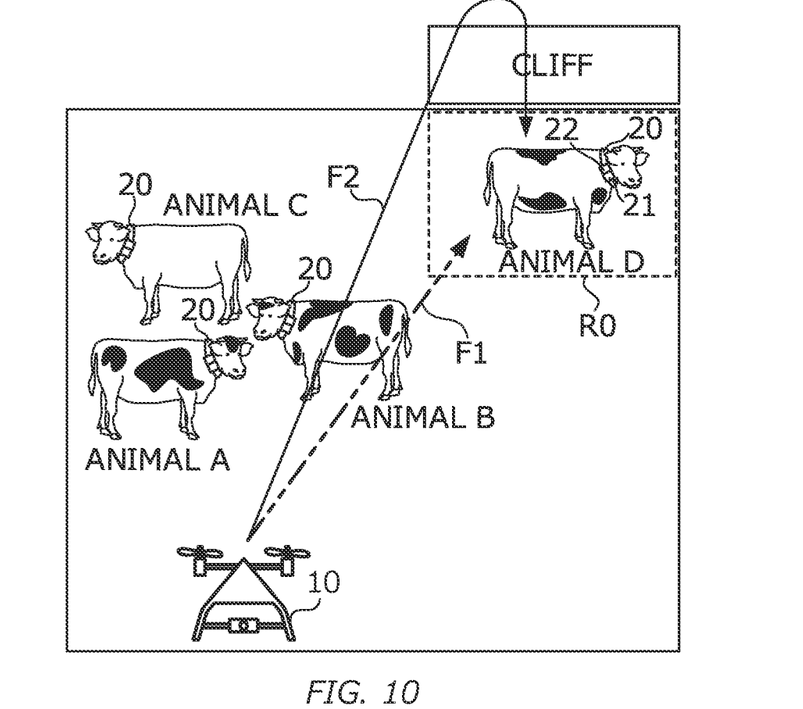
FIG. 10 is a diagram showing an example of a flight path, in accordance to the present invention.

FIG. 10 is a diagram showing an example of a flight path. In this example, assume the case where animal D is the monitoring target. In this case, there are a plurality of candidates for the flight path toward the monitoring position of animal D. Flight path F1 in the diagram is the shortest path toward the monitoring position of animal D among the plurality of candidates. In the case where animal D is not within predetermined range R0 from a cliff, flight path F1 may be set. On the other hand, in the case where animal D is within predetermined range R0 from a cliff, flight path F1 is not set due to being a path toward the monitoring position of animal D in the direction toward the cliff from the position of animal D. In this case, flight path F2 toward the monitoring position of animal D from an opposite direction to the direction toward the cliff from the position of animal D may be set.

Distance setting unit 316 sets the altitude of the position for monitoring an animal, according to the reactivity of the animal targeted for monitoring determined in step S14, based on correspondence table 332 stored in advance in storage 33 (step S16). Also, distance setting unit 316, in the case where the flight path set in step S15 passes over another animal, sets the altitude for when the flight path passes through a predetermined range from the other animal, according to the reactivity of the other animal determined in step S14.

Figure 11:
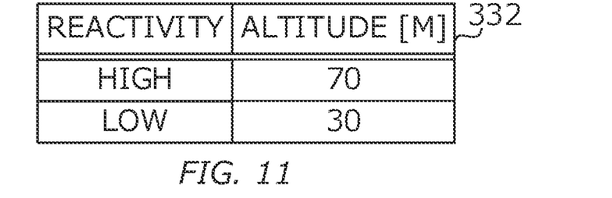
FIG. 11 is a diagram showing an example of correspondence table 332, in accordance to the present invention.

FIG. 11 is a diagram showing an example of correspondence table 332. Correspondence table 332 shows the correspondence relationship between the reactivity of animals and altitude. For example, in the case where the reactivity of animal D targeted for monitoring is "high", altitude "70 m" associated with reactivity "high" is set as the altitude of the monitoring position. On the other hand, in the case where the reactivity of animal D targeted for monitoring is "low", altitude "30 m" associated with reactivity "low" is set as the altitude of the monitoring position. Also, the altitude of the flight path is principally set to "30 m" which is the standard altitude. The standard altitude is the low altitude because this altitude is better for performing the processing for monitoring animals. In the case where, however, the flight path passes over another animal B, as shown in FIG. 10, for example, altitude "70 m" associated with reactivity "high" is set, within the predetermined range from animal B, when the reactivity of animal B is "high", based on correspondence table 332 shown in FIG. 11.

Instruction unit 317 transmits instruction information to flying vehicle 10 instructing to start flying toward the monitoring position, and to perform processing for monitoring the animal on the basis of the monitoring position, in accordance with the flight path and altitude set in steps S15 and S16 (step S17). This instruction information includes path information indicating the flight path set in step S15 and the altitude set in step S16, for example. For example, in the case where animal D is the monitoring target, instruction information instructing to fly to the monitoring position of animal D, along the flight path set in step S15, at the altitude set in step S16 is transmitted. This monitoring position will be a position at the altitude set in step S16 above position "P4" of animal D stored in database 331 shown in FIG. 7, for example. Also, as shown in FIG. 10, in the case where the flight path passes over animal B, this instruction information includes information instructing to fly at the altitude set in step S16 within the predetermined range from animal B.

Figure 12:
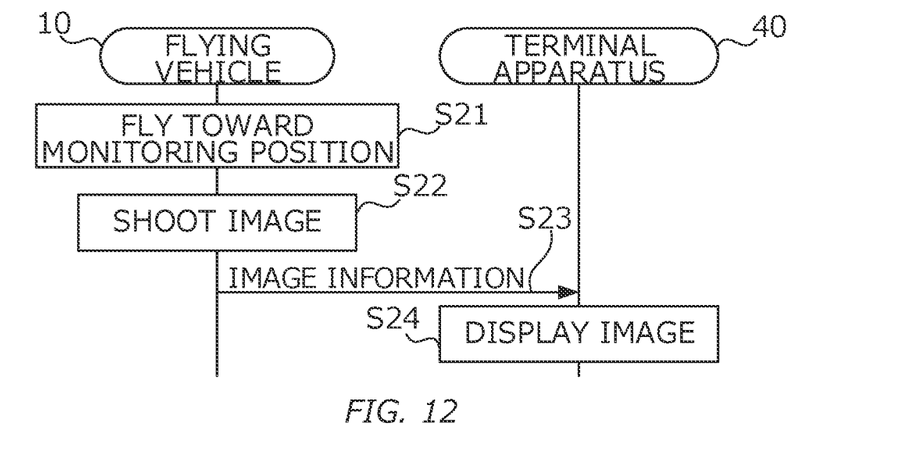
FIG. 12 is a sequence chart showing an example of monitoring processing that is performed by flying vehicle 10 and terminal apparatus 40, in accordance to the present invention.

FIG. 12 is a sequence chart showing an example of monitoring processing that is performed by flying vehicle 10 and terminal apparatus 40. This processing is started in response to flying vehicle 10 receiving instruction information from server apparatus 30.

Flying vehicle 10 starts flying toward the monitoring position, in accordance with the instruction information received from server apparatus 30 (step S21). At this time, flying vehicle 10 navigates automatically without being operated by the manager. Upon arriving at the monitoring position, flying vehicle 10 shoots an image of the animal targeted for monitoring using image capturing apparatus 16 (step S22).

Figure 13:
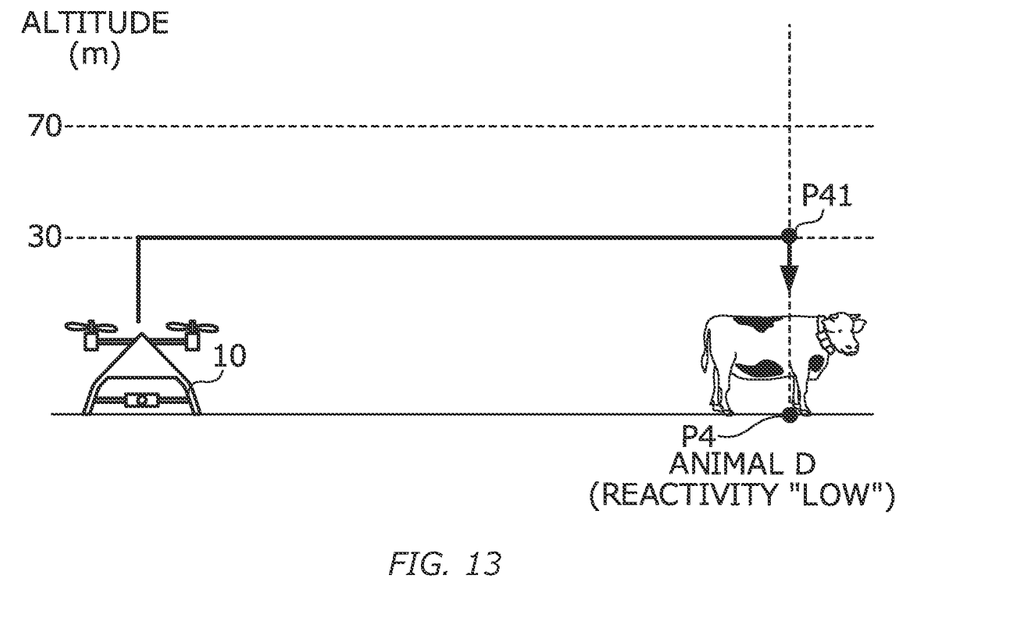
FIG. 13 is a diagram showing an example of the flight altitude of flying vehicle 10, in accordance to the present invention.

FIG. 13 is a diagram showing an example of the flight altitude of flying vehicle 10. In this example, it is assumed that the reactivity of animal D which is the monitoring target is "low" and there are no other animals below the flight path. In this case, flying vehicle 10 ascends to an altitude of 30 m after starting to fly, and flies along the flight path at an altitude of 30 m to monitoring position P41 that is 30 m above position P4 of animal D. Upon arriving at monitoring position P41, flying vehicle 10 descends to a predetermined shooting altitude from monitoring position P41, and shoots an image of animal D. When image shooting is completed, flying vehicle 10 ascends to an altitude of 30 m again, and flies back to the departure position along the same flight path and at the same altitude as the outward leg.

Figure 14:
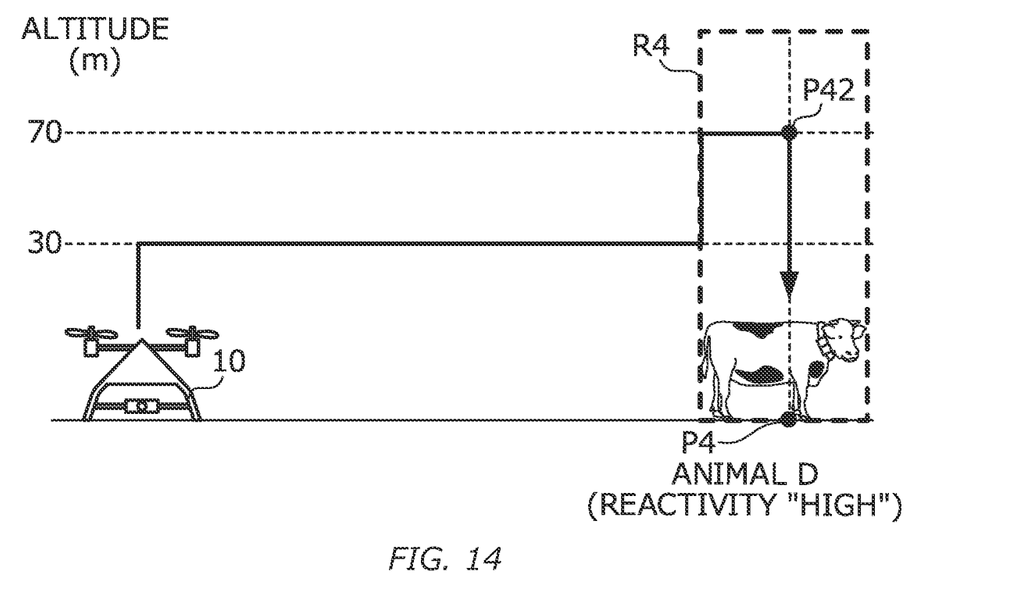
FIG. 14 is a diagram showing another example of the flight altitude of flying vehicle 10, in accordance to the present invention.

FIG. 14 is a diagram showing another example of the flight altitude of flying vehicle 10. In this example, it is assumed that the reactivity of animal D which is the monitoring target is "high" and there are no other animals below the flight path. In this case, flying vehicle 10 ascend to an altitude of 30 m after starting to fly, and flies along the flight path to monitoring position P42 which is 70 m above position P4 of animal D. At this time, flying vehicle 10 flies from position P4 of animal D at an altitude of 30 m outside of predetermined range R4 and, upon entering predetermined range R4, ascends to an altitude of 70 m, and flies at an altitude of 70 m inside of predetermined range R4. Upon arriving at monitoring position P42, flying vehicle 10 descends to the predetermined shooting altitude from monitoring position P42, and shoots an image of animal D. When image shooting is completed, flying vehicle 10 ascends to an altitude of 70 m again, and flies back to the departure position along the same flight path and at the same altitude as the outward leg.

Figure 15:
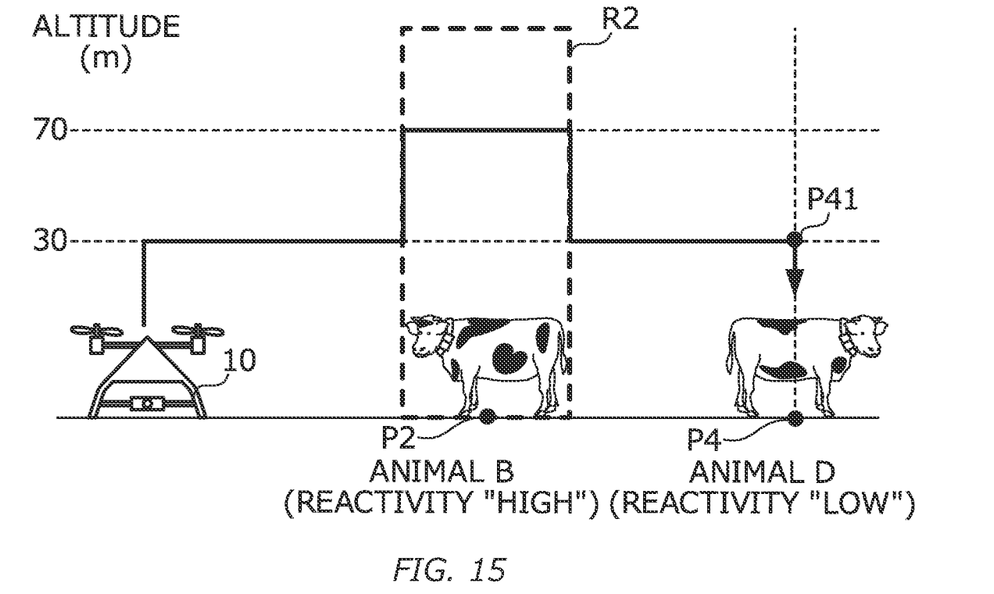
FIG. 15 is a diagram showing another example of the flight altitude of flying vehicle 10, in accordance to the present invention.

FIG. 15 is a diagram showing another example of the flight altitude of flying vehicle 10. In this example, it is assumed that the reactivity of animal D which is the monitoring target is "low" and animal B whose reactivity is "high" is below the flight path. In this case, flying vehicle 10 ascend to an altitude of 30 m after starting to fly, and flies along the flight path to monitoring position P41 which is 30 m above position P4 of animal D. At this time, flying vehicle 10 flies from position P2 of animal B at an altitude of 30 m outside of predetermined range R2 and, upon entering predetermined range R2, ascends to an altitude of 70 m, and flies at an altitude of 70 m inside of predetermined range R2. Upon leaving predetermined range R2, flying vehicle 10 descends to an altitude of 30 m and flies at an altitude of 30 m again. Upon arriving at monitoring position P41, flying vehicle 10 shoots an image of animal D similarly to the example shown in FIG. 13. When image shooting is completed, flying vehicle 10 ascends to an altitude of 30 m again, and flies back to the departure position along the same flight path and at the same altitude as the outward leg.

Returning to FIG. 12, flying vehicle 10 transmits image information indicating the shot image to terminal apparatus 40 (step S23). Transmission of this image information may be performed in real time, for example. Note that "real time" need not necessarily mean simultaneously, and may be at a slight delay. When image information is received from flying vehicle 10, terminal apparatus 40 displays image 461 that is indicated by the received image information on display apparatus 46 (step S24).

Figure 16:
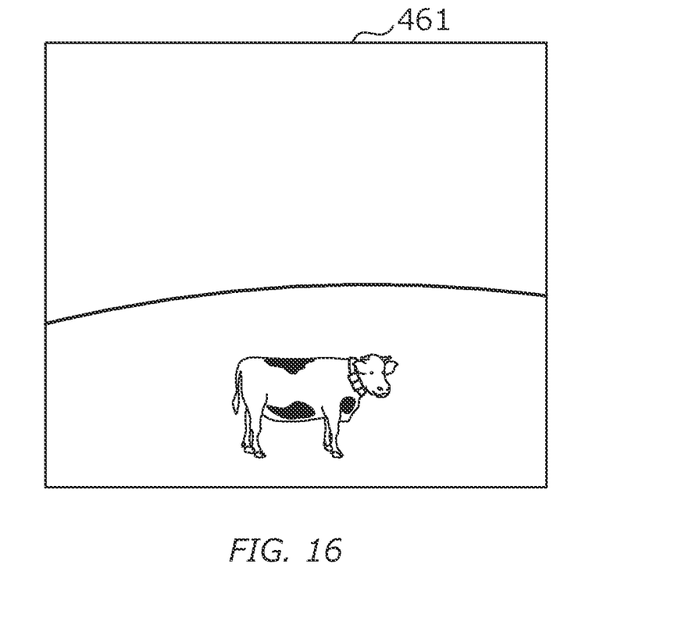
FIG. 16 is a diagram showing an example of image 461 displayed on display apparatus 46, in accordance to the present invention.

FIG. 16 is a diagram showing an example of image 461 displayed on display apparatus 46. This image 461 includes an image of animal D targeted for monitoring. The manager is able to grasp the condition of animal D targeted for monitoring, by viewing this image 461 using terminal apparatus 40. In the case where it is determined that there is an abnormality with animal D, for example, the manager goes to the location of animal D and addresses the problem.

Note that, in the above-described embodiment, "server apparatus 30", "image capturing apparatus 16", the "altitude" of the monitoring position and the "altitude" when passing through a predetermined range from an animal that is below the flight path are respectively used as the "monitoring apparatus", "image capturing unit", "first distance" and "second distance" according to the present invention. Also, "path setting unit 315" and "distance setting unit 316" are both used as a "setting unit" according to the present invention.

In the case of utilizing flying vehicle 10 to perform processing for monitoring animals such as the above-described embodiment, it is better for flying vehicle 10 to fly as low as possible. However, in the case of monitoring animals whose reactivity is high, the animals may be stressed when flying vehicle 10 flies low, due to the presence of flying vehicle 10, the noise emitted by flying vehicle 10, and the like. According to the above-described embodiment, when utilizing flying vehicle 10 to monitor animals whose reactivity is high, monitoring is performed at a distance from the animals, thus enabling the stress of the animals targeted for monitoring to be mitigated. Also, since the reactivity of animals is determined based on the type of animal and the degree of familiarity to flying vehicle 10, a reactivity that reflects these factors can be determined. Furthermore, in the case where other animals with a high reactivity to the approach of flying vehicle 10 are below the flight path toward the monitoring position for monitoring the animal targeted for monitoring, flying vehicle 10 flies at a distance from these animals, thus enabling the stress of other animals to also be mitigated. Furthermore, in the case where the animal targeted for monitoring is within a predetermined range from a predetermined place such as a cliff, a flight path toward the monitoring position from a different direction to the direction toward the predetermined place from the position of the animal is set, thus enabling the animal targeted for monitoring moving to be prevented from moving toward the predetermined place, when flying vehicle 10 moves toward the monitoring position. Furthermore, an image shot of the animal targeted for monitoring is displayed on terminal apparatus 40, thus enabling the manager to see an image of the animal targeted for monitoring.

3. Modifications The present invention is not limited to the above-described embodiment. The above-described embodiment may be modified as follows. Also, two or more of the following modifications may be implemented in combination.

In the above-described embodiment, reactivity may be determined, at the point in time at which flying vehicle 10 approaches an animal in flight. In this case, flying vehicle 10 shoots images of the ground using image capturing apparatus 16 in flight. In the case where flying vehicle 10 flies over an animal, the shot image will include an image of this animal. Determination unit 314 determines the reactivity of the animal by analyzing the image of the animal shot by image capturing apparatus 16. This analysis may include image processing such as edge processing. For example, reactivity "high" may be determined, in the case where, as a result of analyzing the image, a reaction of some sort is recognized, such as the animal being spooked by flying vehicle 10. On the other hand, reactivity "low" may be determined, in the case where, as a result of analyzing the image, such a reaction is not recognized. This processing for determining the reactivity may be performed while flying vehicle 10 is flying back and forth to the monitoring position, or may be performed in advance before performing monitoring processing. Also, in the case where flying vehicle 10 is provided with a voice acquisition apparatus such as a microphone, the reactivity of an animal may be computed by analyzing sounds made by the animal that are acquired by the voice acquisition apparatus, instead of analysis of the image of the animal shot by image capturing apparatus 16 or together with this analysis of the image. For example, reactivity "high" may be determined, in the case where, as a result of analyzing the sounds made by the animal, sounds made by the animal that are agitated or menacing toward flying vehicle 10 are recognized. On the other hand, in the case where, as a result of analyzing the sounds made by the animal, such sounds are not recognized, reactivity "low" may be determined. According to this modification, a reactivity reflecting the situation of the animal when actually approached by flying vehicle 10 can be determined.

In the above-described embodiment, in the case where another animal with high reactivity is close to the animal targeted for monitoring, an altitude corresponding to reactivity "high" may be set, regardless of the reactivity of the animal targeted for monitoring. In this case, distance setting unit 316, in the case where another animal is within a predetermined range from the animal targeted for monitoring, sets an altitude that depends on the reactivity of the other animal as the altitude of the monitoring position. For example, even when the reactivity of the animal targeted for monitoring is "low", in the case where another animal whose reactivity is "high" is within a predetermined range from this animal, the altitude "70 m" associated with reactivity "high" may be set as a reference altitude of the monitoring position. According to this modification, in the case where other animals with a high reactivity to the approach of flying vehicle 10 are around the animal targeted for monitoring, the stress of the other animals can be mitigated.

In the above-described embodiment, the altitude may be lowered, in the case where the urgency of monitoring is high. For example, the urgency of monitoring is considered to be high, in the case where the degree of abnormality of the animal is very high. In this case, the reference altitude of the monitoring position may be 50 m which is lower than the normal 70 m, in the case where the reactivity of the animal targeted for monitoring is "high". According to this modification, in the case where the urgency of monitoring is high, flying vehicle 10 is able to arrive at the monitoring position quickly.

In the above-described embodiment, the altitude of the monitoring position or the altitude of the flight path may be determined based on the reactivity or degree of abnormality of the animal. For example, a value obtained by multiplying the reactivity of the animal by the degree of abnormality may be computed, and the altitude may be higher as this value increases.

In the above-described embodiment, the distance from the position of the animal may be set by changing the altitude. In this case, the monitoring position will be a position that is the set distance from the position of the animal. For example, the monitoring position may be a position that is the set distance diagonally above the position of the animal, or may be a position that is the set distance horizontally from the position of the animal.

In the above-described embodiment, the shooting altitude may be constant, or may change according to the reactivity of the animal. For example, the shooting altitude may be higher as the reactivity of the animal increases.

In the above-described embodiment, the degree of abnormality may be raised, in the case where it is judged that the animal is in a predetermined place, based on the position information acquired by acquisition unit 311. Generally, in the case where there is an abnormality with an animal, the degree of abnormality of the animal gradually increases over time. In this case, it takes a certain amount of time for the degree of abnormality to reach the threshold value. According to this modification, in the case where an animal is in a predetermined place where an abnormality can readily occur or that is potentially dangerous, the timing at which flying vehicle 10 starts flying can be brought forward, since the time taken for the degree of abnormality to reach the threshold value will be short compared with the case where the animal is not in the predetermined place.

In the above-described embodiment, the degree of abnormality may be raised according to the importance of an animal. For example, the importance of an animal may be high, in the case where the animal is a young animal, in the case where the animal is rutting, or in the case where the animal is pregnant. Changing unit 414 may raise the degree of abnormality for an animal with a high importance. According to this modification, the timing at which flying vehicle 10 starts flying can be brought forward for animals with a high importance.

In the above-described embodiment, the shooting method may be changed, according to the type of abnormality of the animal. For example, in the case where the animal is separated from the group, an image may be shot from a higher position than normal, such that the group and the animal may both be shot. Also, in the case where an animal is stationary in the one place, there is possibly an abnormality with the legs, and thus an image is shot focusing on the legs of the animal. According to this modification, the manager is able to more accurately determine the abnormality of the animal by viewing the image of the animal.

In the above-described embodiment, sensor apparatus 20 is not limited to positioning apparatus 21 and biological information sensor 22. Sensor apparatus 20 may include any sensor that detects a physical quantity from an animal. For example, sensor apparatus 20 may include a voice acquisition apparatus such as a microphone. In this case, the degree of abnormality of an animal may be computed, based on voice information indicating sounds made by the animal acquired by the voice acquisition apparatus.

In the above-described embodiment, processing for monitoring an animal is not limited to processing for shooting an image of the animal. For example, the processing for monitoring an animal may be processing for acquiring information such as sounds that the animal makes, processing for suppling something for treating the abnormality to the animal, or processing for tracking the animal.

In the above-described embodiment, the method of measuring the position of an animal is not limited to a method that uses GPS. The position of the animal may be measured with a method that does not use GPS.

In the above-described embodiment or modifications, at least some of the function of server apparatus 30 may be implemented in another apparatus. For example, at least one of acquisition unit 311, computation unit 312, target setting unit 313, determination unit 314, path setting unit 315, distance setting unit 316 and instruction unit 317 may be implemented in terminal apparatus 40.

The present invention may be provided as a method that is provided with processing steps that are performed in monitoring system 1, flying vehicle 10, sensor apparatus 20, server apparatus 30 or terminal apparatus 40. Also, the present invention may be provided as a program that is executed in flying vehicle 10, server apparatus 30 or terminal apparatus 40.

The block diagram of FIG. 5 shows blocks in functional units. These functional blocks (constituent units) can be realized by any combination of hardware and/or software. Also, means for realizing each functional block is not particularly limited. That is, the functional blocks may be respectively realized by single apparatuses that are physically and/or logically coupled, or two or more apparatuses that are physically and/or logically separated may be directly or indirectly (e.g., wire and/or wirelessly) connected, and the functional blocks may be realized by these plurality of apparatuses.

The hardware configuration of flying vehicle 10, server apparatus 30 or terminal apparatus 40 may be constituted so as to include one or more of the apparatuses shown in FIG. 3, 4 or 6, or may be constituted to not include some of the apparatuses. Also, flying vehicle 10, server apparatus 30 or terminal apparatus 40 may be constituted to include hardware such as a microprocessor, a DSP (Digital Signal Processor), an ASIC (Application Specific Integrated Circuit), a PLD (Programmable Logic Device) and a FPGA (Field Programmable Gate Array), or some or all of the functional blocks of flying vehicle 10, server apparatus 30 or terminal apparatus 40 may be realized by such hardware. For example, processor 11, 31 or 41 may be implemented by at least one of such hardware.

Modes/embodiments described in the present description may be applied to a system that utilizes LTE (Long Term Evolution), LTE-A (LTE-Advanced), SUPER 3G, IMT-Advanced, 4G, 5G, FRA (Future Radio Access), W-CDMA (registered trademark), GSM (registered trademark), CDMA2000, UMB (Ultra Mobile Broadband), IEEE 802.11 (Wi-Fi), IEEE 802.16 (WiMAX), IEEE 802.20, UWB (Ultra-WideBand), Bluetooth (registered trademark), and other appropriate systems, and/or to a next generation system extended based on these systems.

The order of processing procedures, sequences, flowcharts and the like of modes/embodiments described in the present description may be rearranged, as long as there are no inconsistencies. For example, with regard to methods described in the present description, the various elements of steps are presented in an illustrative order, and are not limited to the presented specific order.

Input and output information and the like may be saved to a specific location (e.g., memory), or may be managed with a management table. Information and the like that is input and output can be overwritten, updated or added. Output information and the like may be deleted. Input information and the like may be transmitted to another apparatus.

Judgments may be performed depending on a value (0 or 1) represented with 1 bit, may be performed depending a Boolean value (true or false), or may be performed depending a numerical comparison (e.g., comparison with a predetermined value).

Modes/embodiments described in the present description may be used independently, may be used in combination, or may be switched for use in association with execution. Also, notification of predetermined information (e.g., notification of "being X") is not limited to being performed explicitly, and may be performed implicitly (e.g., predetermined information is not notified).

Software, whether referred to as software, firmware, middleware, microcode, a hardware description language or by another name, is intended to be broadly interpreted to mean an instruction, an instruction set, a code, a code segment, a program code, a program, a sub-program, a software module, an application, a software application, a software package, a routine, a subroutine, an object, an executable file, an execution thread, a procedure, a function, and the like.

Also, software, instructions and the like may be transmitted and received via a transmission medium. For example, in the case where software is transmitted from a website, a server or another remote source using a wired technology such as a coaxial cable, a fiber optic cable, a twisted pair cable and a digital subscriber line (DSL) and/or a wireless technology such as infrared rays, wireless and microwaves, such wired technologies and/or wireless technologies are included within the definition of a transmission medium.

Information, signals and the like described in the present description may be represented using one of various different technologies. For example, data, instructions, commands, information, signals, bits, symbols, chips and the like that can be referred to throughout the above description as a whole may be represented by voltages, currents, electromagnetic waves, magnetic fields or magnetic particles, photo fields or photons, or any combination thereof.

The terms "system" and "network" that are used in the present description can be used interchangeably.

Also, information, parameters and the like described in the present description may be represented with an absolute value, may be represented with a relative value from a predetermined value, or may be represented with other corresponding information. For example, a wireless resource may be instructed with an index.

The term "determining" that is used in the present description may encompass a diversity of actions. "Determining" can, for example, include judging, calculating, computing, processing, deriving, investigating, looking up (e.g., looking up a table, a database or another data structure), and ascertaining being regarded as "determining". Also, "determining" can include receiving (e.g., receiving information), transmitting (e.g., transmitting information), input, output, and accessing (e.g., accessing data in memory) being regarded as "determining". Also, "determining" can include resolving, selecting, choosing, establishing, comparing and the like being regarded as "determining". That is, "determining" can include an action of some sort being regarded as "determining".

The phrase "based on" that is used in the present description does not mean "only based on", unless specifically stated otherwise. In other words, the phrase "based on" means both "only based on" and "at least based on".

Any reference to elements using the designations "first", "second" and the like that are used in the present description do not generally limit the amount or order of those elements. These designations can be used in the present description as a convenient method of distinguishing between two or more elements. Accordingly, reference to first and second elements does not mean that only two elements can be employed therein or that the first element must precede the second element in some form or other.

The terms "including", "comprising" and variations thereof, insofar as they are used in the description and claims, are intended to be inclusive, similarly to the term "provided with". Furthermore, the term "or" that is used in the description and claims is not intended to be an exclusive OR.

Throughout the disclosure, in the case where articles are added due to translation, such as "a", "an" and "the" in English, for example, these articles are intended to include the plural form, unless the contrary is clearly indicated from the context.

Although the present invention has been described above in detail, it will be evident to a person skilled in the art that the invention is not limited to the embodiments described in the present description. The present invention can be carried out with corrections and modifications without departing from the spirit and scope of the invention defined in the claims Accordingly, description given herein is illustrative, and is not intended to be interpreted restrictively with respect to the invention.

REFERENCE SIGNS LIST

1 Monitoring system
10 Flying vehicle
11 Processor
12 Memory
13 Storage
14 Communication apparatus
15 Positioning apparatus
16 Image capturing apparatus
20 Sensor apparatus
21 Positioning apparatus
22 Biological information Sensor
30 Server apparatus
40 Terminal apparatus
311 Acquisition unit
312 Computation unit
313 Target setting unit
314 Determination unit
315 Path setting unit
316 Distance setting unit
317 Instruction unit

What is claimed is:
1. A monitoring apparatus comprising:
an acquisition unit that acquires position information indicating a position of a subject animal;
a determination unit that determines a reactivity of the subject animal to an approach of a flying vehicle within a predetermined range from the position of the subject animal;
a setting unit that sets a flight path of the flying vehicle depending on the determined reactivity of the subject animal, the flight path proceeding from an initial position at a first altitude to a monitoring position at a second altitude proximate to the position of the subject animal, and then descends to a processing position for monitoring the subject animal at a third altitude, wherein the flight path transitions to the second altitude when the flying vehicle is within the predetermined range from the position of the subject animal, and wherein the second altitude is greater than the first altitude when the determined reactivity of the subject animal at least meets a predetermined criterion to mitigate stress of the subject animal; and
an instruction unit that instructs the flying vehicle to fly according to the set flight path to the monitoring position that is proximate the position of the subject animal being monitored, and to perform processing for monitoring the subject animal at the processing position, to acquire information of the subject animal that is used by a manager to determine whether there is an abnormality with the subject animal.

2. The monitoring apparatus according to claim 1,
wherein the setting unit increases the second altitude as the determined reactivity of the subject animal increases, and
the monitoring position is a position that is the set second altitude from the position indicated by the acquired position information of the subject animal.

3. The monitoring apparatus according to claim 1,
wherein the determination unit determines the reactivity of the subject animal, according to a type of the subject animal or a degree of familiarity of the subject animal to the flying vehicle.

4. The monitoring apparatus according to claim 1,
wherein the determination unit determines the reactivity of the subject animal, by analyzing an image of the subject animal captured by an image capturing unit disposed on the flying vehicle.

5. The monitoring apparatus according to claim 1,
wherein the acquisition unit further acquires position information indicating a position of a second animal;
wherein the determination unit further determines a reactivity of the second animal to an approach of the flying vehicle within a predetermined range from the position of the second animal;
wherein, in a case where the flight path of the flying vehicle passes through the predetermined range from the position of the second animal, the setting unit further sets the flight path to a fourth altitude when the flying vehicle is within the predetermined range from the position of the second animal, wherein the fourth altitude depends on the determined reactivity of the second animal, and wherein the fourth altitude is greater than the first altitude when the determined reactivity of the second animal at least meets the predetermined criterion to mitigate stress of the second animal; and
an instruction unit that instructs the flying vehicle to fly according to the set flight path to the monitoring position, wherein the second animal is located below the flight path to the monitoring position.

6. The monitoring apparatus according to claim 1,
wherein the acquisition unit further acquires position information indicating a position of a second animal;
wherein the determination unit further determines a reactivity of the second animal to an approach of the flying vehicle within a predetermined range from the position of the second animal;
wherein, in a case where the second animal is within a predetermined range from the subject animal, the setting unit further sets the flight path to a fourth altitude when the flying vehicle is within the predetermined range from the positions of the subject animal and the second animal, wherein the fourth altitude depends on the greatest determined reactivity of the subject animal and second animal, wherein the fourth altitude is greater than the first altitude when the determined reactivity of at least one of the subject animal and second animal at least meets the predetermined criterion to mitigate stress of the subject animal and the second animal; and
an instruction unit that instructs the flying vehicle to fly according to the set flight path to the monitoring position, wherein the second animal is located below the flight path to the monitoring position.

7. The monitoring apparatus according to claim 1,
wherein the setting unit, in a case where it is judged that the subject animal is within a predetermined range from a predetermined place, based on the acquired position information of the subject animal, sets a flight path toward the monitoring position passing over the predetermined place prior to reaching the monitoring position.

8. The monitoring apparatus according to claim 1,
wherein the processing performed by the instruction unit includes capturing an image of the subject animal with an image capturing unit disposed on the flying vehicle.

9. The monitoring apparatus according to claim 1,
wherein the reactivity of the subject animal to an approach of the flying vehicle determined by the determination unit decreases with an increase of a degree of familiarity of the subject animal with the flying vehicle.

10. The monitoring apparatus according to claim 9,
wherein the familiarity of the subject animal with the flying vehicle is based on at least one of a number of times the flying vehicle has approached the subject animal and a time period the subject animal has been at the monitoring position.

11. The monitoring apparatus according to claim 1,
wherein the reactivity of the subject animal to an approach of the flying vehicle determined by the determination unit is determined as the flying vehicle approaches the subject animal.

12. The monitoring apparatus according to claim 11,
wherein, as the flying vehicle approaches the subject animal, the determination unit determines the reactivity of the subject animal is determined based on at least one of an image captured and a sound recorded of the subject animal as the flying vehicle approaches the subject animal.

13. The monitoring apparatus according to claim 12,
wherein the determination unit determines a first reactivity when the animal reacted to the flying vehicle, which is a result of analyzing the acquired information; and
wherein the determination unit determines a second reactivity that is lower than the first reactivity when no reaction of the animal is detected, which is a result of analyzing the acquired information.

14. The monitoring apparatus according to claim 1,
wherein the setting unit sets the second altitude based on the reactivity of the subject animal and a degree of abnormality of the subject animal.

15. The monitoring apparatus according to claim 14,
wherein the second altitude is greater based on the greater degree of abnormality of the subject animal.

16. The monitoring apparatus according to claim 14,
wherein the acquisition unit further acquires data indicative of the degree of abnormality of the subject animal from a sensor attached to the subject animal.

17. The monitoring apparatus according to claim 14, further comprising:
a computation unit that determines the degree of abnormality of the subject animal based on the acquired position information of the subject animal.

18. The monitoring apparatus according to claim 1,
wherein the second altitude is no greater than the first altitude when the determined reactivity of the subject animal at least meets another predetermined criterion.

19. The monitoring apparatus according to claim 1,
wherein the third altitude is less than the first altitude and second altitude.

20. A program stored on a non-transitory computer-readable recording medium for causing a processor to execute:
acquiring position information indicating a position of a subject animals;
determining a reactivity of the subject animal to an approach of a flying vehicle within a predetermined range from the position of the subject animal;
setting a flight path of the flying vehicle depending on the determined reactivity of the subject animal, the flight path proceeding from an initial position at a first altitude to a monitoring position at a second altitude proximate to the position of the subject animal, and then descends to a processing position for monitoring the subject animal at a third altitude, wherein the flight path transitions to the second altitude when the flying vehicle is within the predetermined range from the position of the subject animal, and wherein the second altitude is greater than the first altitude when the determined reactivity of the subject animal at least meets a predetermined criterion to mitigate stress of the subject animal; and
instructing the flying vehicle to flying vehicle to fly according to the set flight path to the monitoring position that is proximate the position of the subject animal being monitored, and to perform processing for monitoring the subject animal at the processing position, to acquire information of the subject animal that is used by a manager to determine whether there is an abnormality with the subject animal.

* * * * *

UNITED STATES PATENT AND TRADEMARK OFFICE
CERTIFICATE OF CORRECTION

| | | |
|---|---|---|
| PATENT NO. | : 11,432,534 B2 | |
| APPLICATION NO. | : 17/056833 | |
| DATED | : September 6, 2022 | |
| INVENTOR(S) | : Naoki Kameyama et al. | |

It is certified that error appears in the above-identified patent and that said Letters Patent is hereby corrected as shown below:

In the Claims

- Column 18, Line 52, Claim 20 delete the words "to flying vehicle".

Signed and Sealed this
Eighth Day of November, 2022

*Katherine Kelly Vidal*

Katherine Kelly Vidal
*Director of the United States Patent and Trademark Office*